United States Patent [19]

Kaugars

[11] 4,160,037

[45] Jul. 3, 1979

[54] COMPOUNDS, COMPOSITIONS AND METHODS OF COMBATTING PEST EMPLOYING THIOUREAS

[75] Inventor: Girts Kaugars, Cooper Township, Kalamazoo County, Mich.

[73] Assignee: The Upjohn Company, Kalamazoo, Mich.

[21] Appl. No.: 838,165

[22] Filed: Sep. 30, 1977

[51] Int. Cl.$^2$ ...................... A01N 9/12; C07C 157/07
[52] U.S. Cl. .................................. 424/322; 260/552 R
[58] Field of Search ...................... 424/322; 260/552 R

[56] References Cited

U.S. PATENT DOCUMENTS

| | | | |
|---|---|---|---|
| 3,748,356 | 7/1973 | Wellinga et al. | 260/553 E |
| 3,892,864 | 7/1975 | Yamamoto et al. | 424/322 |

FOREIGN PATENT DOCUMENTS

| | | | |
|---|---|---|---|
| 74262 | 7/1970 | Fed. Rep. of Germany | 260/552 R |
| 45-15518 | 5/1970 | Japan | 424/322 |
| 46-28116 | 8/1971 | Japan | 424/322 |
| 1099767 | 11/1968 | United Kingdom. | |

OTHER PUBLICATIONS

Wellinga et al., J. Agr. Food Chem., vol. 21, No. 3, (1973) pp. 348–354.
Yu et al., J. Agr. Food Chem., vol. 24, No. 1 (1976) pp. 134–136.
Wellinga et al., J. Agr. Food Chem., vol. 21, No. 6 (1973) pp. 993–998.

*Primary Examiner*—Allen J. Robinson
*Attorney, Agent, or Firm*—Sidney B. Williams, Jr.

[57] ABSTRACT

3-Benzoyl-1-phenyl-2-thioureas are disclosed as insecticides, miticides and nematicides.

9 Claims, No Drawings

COMPOUNDS, COMPOSITIONS AND METHODS OF COMBATTING PEST EMPLOYING THIOUREAS

SUMMARY OF THE INVENTION

This invention pertains to some new organic compounds, to a process for preparing them and to formulations of them suitable for pesticidal use. The invention is more particularly directed to 3-benzoyl-1-phenyl-2-thioureas that have halogen and alkyl substituents attached at selective places on the molecule thereby imparting outstanding insecticidal properties to the molecule.

3-benzoyl-1-phenyl-2-thioureas are known and U.S. Pat. No. 3,748,356, British Pat. No. 1,099,767, C. C. Yu et al., J. Agr. Food Chem., 24, 134–136 (1976), Wellinga et al., J. Agr. Food Chem., 21 (1973), pp. 348–354 and 993–998 can be referred to as relevant status of art. However, insofar as is presently known, no one has either prepared applicants 3-benzoyl-1-phenyl-2-thiourea or suggested that they would have superior insecticidal properties.

In general, the prior art teaches that insecticidal and/or larvicidal activity is enhanced by the presence of ortho substituents on the benzoyl moiety. Applicants novel compounds, are free of ortho substituents on the benzoyl ring, yet they exhibit good insecticidal activity.

DETAILED DESCRIPTION OF THE INVENTION

The 3-benzoyl-1-phenyl-2-thiourea of this invention are represented by the formula

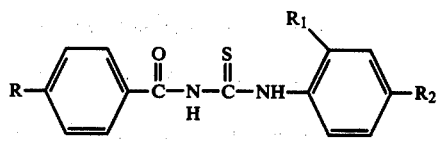

wherein R is selected from the group consisting of hydrogen, bromo, and chloro; and $R_1$ and $R_2$ are the same or different and are selected from the group consisting of bromo, chloro, and lower alkyl of from one to four carbon atoms, inclusive.

In the foregoing designation of variables, "lower alkyl" means methyl, ethyl, propyl, butyl and the isomeric forms thereof.

The new 3-benzoyl-1-thioureas are readily prepared using known procedures or slight modifications, thereof from inexpensive known starting materials in accordance with the following schematic representation:

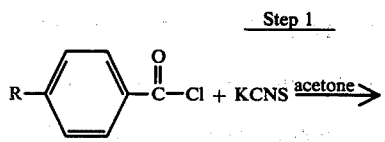

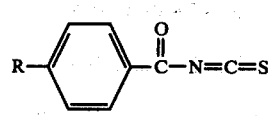

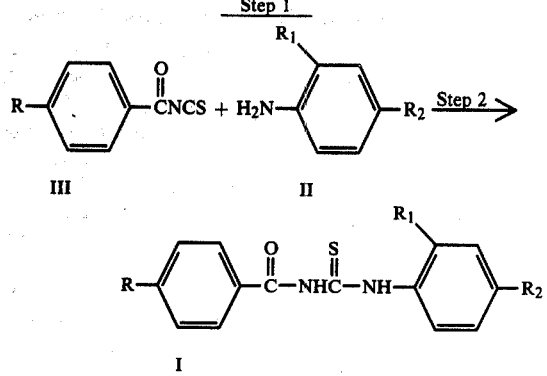

wherein R, $R_1$, and $R_2$ are the same as above.

The substituted benzoyl chlorides of formula IV are readily available as are the substituted anilines of formula II.

Step 1 is effected by reacting the benzoyl chloride with potassium thiocyanate in the presence of an organic solvent at about 0° to 100° C. illustrative of the solvents are acetone, methyl ethyl ketone, acetonitrile. Acetone is a particularly effective solvent.

The benzoylisothiocyanate III is recovered by conventional methods such as filtration, solvent evaporation, distillation, chromatography, crystallization and/or combinations thereof.

Step 2 is conducted by reacting the benzoylisothiocyanate III with a substituted aniline II at a temperature of about 0° C. to 100° C. in the presence of an organic solvent. Effective solvents are acetone, tetrahydrofuran, toluene, chloroform with acetone again being particularly effective.

The preferred compounds of this invention are those having the formula

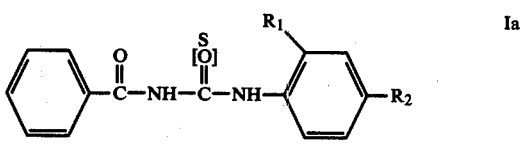

wherein $R_1$ is alkyl of from 1 to 4 carbon atoms, inclusive, and $R_2$ is selected from the group consisting of bromo and chloro.

The following described preparations of new compounds according to formula I are indicative of the scope of this invention and are not to be construed as limitive. Those skilled in the art will promptly recognize appropriate variations from the procedure both as to starting materials as well as reaction conditions and techniques. These examples indicate the best mode presently known to the inventor.

PREPARATION 1: Reactant benzoylisothiocyanate

To 99.1 g. (1.02 moles) of potassium thiocyanate in 1 l. of acetone is added 140.6 g. (1.00 mole) of benzoyl chloride. The suspension is refluxed for 5 minutes, cooled to 20° and filtered. The solids are washed with 300 ml. of acetone, the combined filtrates evaporated to dryness, and the residue distilled to yield 115.5 g. (70.8%) of benzoylisothiocyanate, b. p. 86°–89°/0.65 mm.

EXAMPLE 1: Preparation of the compound 3-benzoyl-1-(4-chloro-2-methylphenyl)-2-thiourea To a refluxing suspension of benzoylisothiocyanate prepared by mixing 53.4 g. (0.55 mole) of potassium thiocynate in 250 ml. of acetone with 70.3 g. (0.50 mole) of benzoyl chloride, which is added dropwise, is added a solution of 70.8 g. (0.500 mole) of 4-chloro-o-toluidine in 200 ml. of acetone at a rate to maintain reflux. The resulting suspension is refluxed for 0.5 hour and then poured into 1.5 l. of ice water. The precipitate is collected, washed with water and dissolved in chloroform. The solution is dried with sodium sulfate and evaporated to dryness to yield 151.4 g. (99.3%) of product. Recrystallization of 30.0 g. of this product from 1:1 benzene/cyclohexane yields 25.1 g. of 3-benzoyl-1-(4-chloro-2-methylphenyl)-2-thiourea, m.p. 148.0° C.

Analysis: Calcd. for $C_{15}H_{13}ClN_2OS$: C, 59.11; H, 4.30; N, 9.19 Found: C, 59.34; H, 4.26; N, 9.21.

EXAMPLE 2

Starting with the compound benzoylisothiocyanate, as prepared in Preparation 1, and the appropriate 2-alkyl-4-chloro or 4-bromo substituted aniline, the following compounds are prepared by procedures similar to Example 1

3-benzoyl-1-(4-chloro-2-ethylphenyl)-2-thiourea,
3-benzoyl-1-(4-chloro-2-propylphenyl)-2-thiourea,
3-benzoyl-1-(4-chloro-2-isopropylphenyl)-2-thiourea,
3-benzoyl-1-(4-chloro-2-n-butylphenyl)-2-thiourea,
3-benzoyl-1-(4-chloro-2-sec-butylphenyl)-2-thiourea,
3-benzoyl-1-(4-chloro-2-t-butylphenyl)-2-thiourea,
3-benzoyl-1-(4-bromo-2-ethylphenyl)-2-thiourea,
3-benzoyl-1-(4-bromo-2-propylphenyl)-2-thiourea,
3-benzoyl-1-(4-bromo-2-isopropylphenyl)-2-thiourea,
3-benzoyl-1-(4-bromo-2-n-butylphenyl)-2-thiourea,
3-benzoyl-1-(4-bromo-2-sec-butylphenyl)-2-thiourea,
3-benzoyl-1-(4-bromo-2-t-butylphenyl)-2-thiourea,

EXAMPLE 3: Preparation of the compound 3-benzoyl-1-(4-bromo-2-methylphenyl)-2-thiourea To 4.20 g. (25.7 mmoles) of benzoylisothiocyanate in 100 ml. of acetone is added 4.65 g. (25.0 mmoles) of 4-bromo-2-methyl aniline. The solution is refluxed for 20 minutes and poured into ice water. The precipitate is collected and recrystallized from ethanol/benzene to yield 7.848 (89.8%) of 3-benzoyl-1-(4-bromo-2-methylphenyl)-[2-thiourea, mp. 157.1° C.

Analysis: Calcd. for $C_{15}H_{13}BrN_2O_5$: C, 51.59: H, 3.75; H, 8.02. Found: C, 51.75; H, 3.87; N, 7.83.

EXAMPLE 4

Starting with the compound benzoylisothiocyanate as prepared in Preparation 1 and the appropriate 2-alkyl-4-haloaniline, the following compounds are prepared by procedures similar to Example 3.

3-benzoyl-1-(4-bromo-2-ethylphenyl)-2-thiourea,
3-benzoyl-1-(4-bromo-2-propylphenyl)-2-thiourea,
3-benzoyl-1-(4-bromo-2-isopropylphenyl)-2-thiourea,
3-benzoyl-1-(4-bromo-2-n-butylphenyl)-2-thiourea,
3-benzoyl-1-(4-bromo-2-sec-butylphenyl)-2-thiourea,
3-benzoyl-1-(4-bromo-2-tert-butylphenyl)-2-thiourea,
3-benzoyl-1-(4-chloro-2-ethylphenyl)-2-thiourea,
3-benzoyl-1-(4-chloro-2-propylphenyl)-2-thiourea,
3-benzoyl-1-(4-chloro-2-isopropylphenyl)-2-thiourea,
3-benzoyl-1-(4-chloro-2-n-butylphenyl)-2-thiourea,
3-benzoyl-1-(4-chloro-2-sec-butylphenyl)-2-thiourea,
3-benzoyl-1-(4-chloro-2-t-butylphenyl)-2-thiourea.

EXAMPLE 5: Preparation of the compound 3-(4-chlorobenzoyl)-1-(2-methyl-4-chlorophenyl)-2-thiourea To a refluxing solution 4-chlorobenzoylisothiocyanate prepared by mixing 5.34 g. (0.055 mole) of potassium thiocyanate in 60 ml. of acetone with 8.75 g. (0.050 mole) of p-chlorobenzoyl chloride, which is added dropwise, is added 7.08 g. (0.050 mole) of 2-methyl-4-chloro-aniline. The solution is refluxed 20 minutes and poured into ice water. The precipitate is collected and recrystallized from ethanol:benzene to yield 12.90 g. (76.1%) of 3-(4-chlorobenzoyl)-1-(2-methyl-4-chlorophenyl)-2-thiourea m.p. 162.6° C.

Analysis: Calcd. for $C_{15}H_{12}Cl_2N_2O_5$: C, 53.11; H, 3.57; N, 8.26. Found: C, 53.21; H, 3.59; N, 8.45.

EXAMPLE 6

Starting with the appropriate 4-halo-benzoylisothiocyanate and the appropriate 2-alkyl-4-haloaniline, the following compounds are prepared by procedures similar to Example 5.

3-(4-chlorobenzoyl)-1-(2-ethyl-4-chlorophenyl)-2-thiourea,
3-(4-chlorobenzoyl)-1-(2-propyl-4-chlorophenyl)-2-thiourea,
3-(4-chlorobenzoyl)-1-(2-isopropyl-4-chlorophenyl)-2-thiourea,
3-(4-chlorobenzoyl)-1-(2-n-butyl-4-chlorophenyl)-2-thiourea,
3-(4-chlorobenzoyl)-1-(2-sec-butyl-4-chlorophenyl)-2-thiourea,
3-(4-chlorobenzoyl)-1-(2-t-butyl-4-chlorophenyl)-2-thiourea,
3-(4-chlorbenzoyl)-1-(2-methyl-4-bromophenyl)-2-thiourea,
3-(4-chlorobenzoyl)-1-(2-ethyl-4-bromophenyl)-2-thiourea,
3-(4-chlorobenzoyl)-1-(2-propyl-4-bromophenyl)-2-thiourea,
3-(4-chlorobenzoyl)-1-(2-isopropyl-4-bromophenyl)-2-thiourea,
3-(4-chlorobenoyl)-1-(2-n-butyl-4-bromophenyl)-2-thiourea,
3-(4-chlorobenzoyl)-1-(2-sec-butyl-4-bromophenyl)-2-thiourea,
3-(4-chlorobenzoyl)-1-(2-t-butyl-4-bromophenyl)-2-thiourea,
3-(4-bromophenyl)-1-(2-methyl-4-chlorophenyl)-2-thiourea,
3-(4-bromophenyl)-1-(2-ethyl-4-chlorophenyl)-2-thiourea,
3-(4-bromophenyl)-1-(2-propyl-4-chlorophenyl)-2-thiourea,
3-(4-bromophenyl)-1-(2-isopropyl-4-chlorophenyl)-2-thiourea,
3-(4-bromophenyl)-1-(2-n-butyl-4-chlorophenyl)-2-thiourea,
3-(4-bromophenyl)-1-(2-sec-butyl-4-chlorophenyl)-2-thiourea,
3-(4-bromophenyl)-1-(2-t-butyl-4-chlorophenyl)-2-thiourea,
3-(4-bromophenyl)-1-(2-methyl-4-bromophenyl)-2-thiourea, 3-(4-bromophenyl)-1-(2-ethyl-4-bromophenyl)-2-thiourea,
3-(4-bromophenyl)-1-(2-propyl-4-bromophenyl)-2-thiourea,
3-(4-bromophenyl)-1-(2-isopropyl-4-bromophenyl)-2-thiourea,
3-(4-bromophenyl)-1-(2-n-butyl-4-bromophenyl)-2-thiourea,
3-(4-bromophenyl)-1-(2-sec-butyl-4-bromophenyl)-2-thiourea,
3-(4-bromophenyl)-1-(2-t-butyl-4-bromophenyl)-2-thiourea.

EXAMPLE 7.

Preparation of the compound 3-benzoyl-1-(2,4-dichlorophenyl)-2-thiourea.

To a refluxing solution of benzoylisothiocyanate prepared by mixing 5.34 g. (0.055 mole) of potassium thiocyanate in 50 ml. of acetone with 7.03 g. (0.050 mole) of benzoyl chloride, which is added dropwise, is added 8.10 g. (0.050 mole) of 2,4-dichloraniline. The solution is refluxed 5 minutes and poured into water. The precipitate is collected by filtration and recrystallized from benzene:ethanol to yield 13.0 g. (80.0%) of 3-benzoyl-1-(2,4-dichlorophenyl)-2-thiourea, m.p. 151° C.

Analysis: Calcd. for $C_{14}H_{10}Cl_2N_2O_5$: C, 51.71; H, 3.10; N, 8.01. Found: C, 51.76; H, 3.20; N, 8.62.

Starting with benzoylisothiocyanate and the appropriate 2,4-dihaloaniline, the following compounds are prepared by procedures similar to Example 7.
p0 3-benzoyl-1-(2,4-dibromophenyl)-2-thiourea,
3-benzoyl-1-(2-bromo-4-chlorophenyl)-2-thiourea,
3-benzoyl-1-(4-bromo-2-chlorophenyl)-2-thiourea.

EXAMPLE 8: Preparation of the compound 3-benzoyl-1-(2-chloro-4-methylphenyl)-2-thiourea To a refluxing solution of benzoylisothiocyanate prepared by mixing 5.34 g. (0.055 mole) of potassium thiocyanate in 50 ml. of acetone with 7.03 g. (0.050 mole) of benzoyl chloride, which is added dropwise, is added 7.08 g. (0.050 mole) of 2-chloro-4-methylaniline. The solution is refluxed for 10 minutes, stirred at room temperature overnight and then poured into water. The precipitate is collected by filtration and recrystallized from ethanol to yield 12.31 g. (80.8%) of 3-benzoyl-1-(2-chloro-4-methylphenyl)-2-thiourea, m.p. 143.4° C.

Analysis: Calcd. for $C_{15}H_{13}ClN_2O_5$: C, 59.11; H, 4.30; N, 9.19. Found: C, 59.03; H, 4.32; N, 9.28.

EXAMPLE 9

Starting with the compound benzoylisothiocyanate as prepared in Preparation 1 and the appropriate 4-alkyl-2-halo aniline, the following compounds are prepared by procedures similar to Example 3.

3-benzoyl-1-(2-bromo-4-ethylphenyl)-2-thiourea,
3-benzoyl-1-(2-bromo-4-propylphenyl)-2-thiourea,
3-benzoyl-1-(2-bromo-4-isopropylphenyl)-2-thiourea,
3-benzoyl-1-(2-bromo-4-n-butylphenyl)-2-thiourea,
3-benzoyl-(1-(2-bromo-4-sec-butylphenyl)-2-thiourea,
3-benzoyl-1-(2-bromo-4-tert-butylphenyl)-2-thiourea,
3-benzoyl-1-(2-chloro-4-ethylphenyl)-2-thiourea,
3-benzoyl-1-(2-chloro-4-propylphenyl)-2-thiourea,
3-benzoyl-1-(2-chloro-4-isopropylphenyl)-2-thiourea,
3-benzoyl-1(2-chloro-4-n-butylphenyl)-2-thiourea,
3-benzoyl-1-(2-chloro-4-sec-butylphenyl)-2-thiourea,
3-benzoyl-1-(2-chloro-4-t-butylphenyl)-2-thiourea,
3-benzoyl-1-(2-bromo-4-methylphenyl)-2-thiourea.

The compounds of formula I are effective pesticides that can be used to control invertebrate pests in argiculture, industry and around the home. For example, the compounds 3-benzoyl-1-(4-chloro-2-methylphenyl)-2-thiourea and 3-benzoyl-1-(4-bromo-2-methylphenyl)-2-thiourea are effective against the cabbage looper (*Trichoplusia ni*) at concentration as low as 3.3 ppm.

Some invertebrate animal pests will be more sensitive to the compounds than others, and others might be quite resistant. In general, the compounds of Formula I are used at concentrations ranging from about 1 to about 5000 ppm.

For practical application, these compounds can be made into formulations comprising a diluent carrier with or without adjuvants that will promote the distribution of the active compounds where pest control is desired and thus enhance efficacy and economics.

There are many different kinds of diluent carriers suitable for the method and formulation embodiments of this invention. Dispersible carriers are commonly used in the art. Such carriers may or may not include adjuvants such as wetting agents, emulsifying agents, stickers, and other components that indirectly promote efficacy.

The new 3-benzoyl-1-aryl-2-thioureas of Formula I are useful against insects, nematodes, and mites in formulations, e.g., as dusts, wettable powders, emulsifiable concentrates, aqueous dispersions, solutions, and flowable creams for application to a situs, soil, plants, and foliage, seeds, or other parts of plants. Granular formulations can be prepared and applied to soil or on surfaces. Moreover, the new compounds of Formula (I) of this invention can be the sole active agent in a formulation or other insecticidal, miticidal, or nematicidal components may be included.

The new compounds of formula (I) can be readily formulated as dusts by grinding a mixture of the compound and a pulverulent carrier in the presence of each other. Grinding is conveniently accomplished in a ball mill, a hammermill, or by air-blast micronization. A suitable ultimate particle size is less than 60 microns. Preferably, 95% of the particles are less than 50 microns, and about 75% are 5 to 20 microns. Dusts of that degree of comminution are conveniently free-flowing and can be applied to animals, inanimate matter, fruit trees, crop plants, and soil so as to effect thorough distribution and coverage. Dusts are particularly adapted for effectively controlling insects and mites over wide areas when applied by airplane. They are also indicated for application to the undersides of plant foliage.

Representative suitable pulverulent carriers include the natural clays such as China, Georgia, Barden, Attapulgus, Koalin, and Bentonite clays; minerals in their natural forms as they are obtained from the earth such as talc, pyrophillite, quartz, diatomaceous earth, Fuller's earth, chalk, sulfur, silica and silicates; chemically modified minerals such as washed bentonite and colloidal silica; and organic flours such as wood, walnut shell, soybean, cottonseed, and tobacco flours, and free-flowing, hydrophobic starches.

Dusts can also be prepared by dissolving the 3-benzoyl-1-phenyl-2-thioureas pesticides of Formula I in a volatile solvent such as methyl chloride, mixing the solution with a pulverulent carrier and evaporating the solvent.

The proportions of pulverulent carrier and active compound (Formula I) can vary over a wide range depending upon the use of it, insect, nematode or mite pests to be controlled, and the conditions of treatment. In general, dust formulations can contain up to about 90% (on a weight basis) of the active ingredient.

The dispersible powder formulations of this invention are prepared by incorporating a surfactant in a dust formulation prepared as described above. When about 0.1% to about 12% of a surfactant is incorporated in a dust, the dispersible powder thus obtained is particularly adapted for further admixture with water for spraying on inamimate matter and products, fruit trees, field crops, soil, and livestock. The dispersible powders can be admixed with water to obtain any desired concentration of active ingredient, and the mixture can be applied in amounts sufficient to obtain predetermined rates of application and uniform distribution. With this flexibility in mind, the dispersible powders of the invention can conveniently comprise preferably about 5% to about 80% of active ingredient.

Representative surfactants useful for preparing dispersible powder formulations of this invention include alkyl sulfates and sulfonates, alkyl aryl sulfonates, sulfosuccinate esters, polyoxyethylene sulfates, polyoxyethylene sorbitan monolaurate, alkyl aryl polyether sulfates, alkyl aryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids, lignin sulfonates, and the like. The preferred class of surfactants includes blends of sulfonated oils and polyalcohol carboxylic acid esters (Encol H-77), blends of polyethoxy ethanols (Tritons X-151, X-161, X-171), e.g., about equal parts of sodium kerylbenzene sulfonate and isooctylphenoxy polyethoxy ethanol containing about 12 ethoxy groups, and blends of calcium alkyl aryl sulfonates and polyethoxylated vegetable oils (Agrimul N$_2$S). It will be understood, of course, that the sulfate and sulfonate surfactants suggested above will preferably be used in the form of their soluble salts, for example, their sodium salts. All of these surfactants are capable of reducing the surface tension of water in concentrations of about 1% or less. The dispersible powder formulations can be prepared with a mixture of surfactants of the types indicated if desired.

A suitable dispersible powder formulation is obtained by blending and milling 191 lbs. of Barden Clay, 23 sugar free sodium lignosulfonate Lignasol SFX) as a dispersing agent, 14 lbs. of sodium alkylnaphthalene sulfonate (NeKal BA77) as a wetting agent, and 227 lbs. of the active ingredient, e.g, the compound embodiment of Example 1. The resulting formulation has the following percentage composition (parts herein are by weight unless otherwise specified).

Active Ingredient: 50%
Lignolsl SFX: 5%
Nekal BA-77: 3%
Barden Clay: 42%

This formulation, when dispersed in water at the rate of 2 lbs. per 100 gals., gives a spray formulation containing about 0.12% (1200 ppm) active ingredient which can be applied against insects, or mites, on plants, fruit trees, or other habitats, or can be used to spray soil against nematodes.

If desired, dispersants such as methylcellulose polyvinyl alcohol, sodium ligninsulfonates, and the like can be included in the dispersible powder formulations of this invention. Adhesive or sticking agents such as vegetable oils, naturally occuring gums, casein, Zonarez B, a series of polymerized terpenes, Unirez 709, a maleic acid-derived resin, Polypole, partially dimerized resin acids, and Dymerex, a dimeric resin acid, and others can also be included. Corrosion inhibitors such as epichlorohydrin and anti-foaming agents such as stearic acid can also be included. Methods for including these agents in pesticidal formulations are well-known in the art and are applicable to this invention.

The new compound of Formula I of this invention can also be applied to insects, mites, objects, or situs in aqueous sprays without a solid carrier. Since, however, the compounds themselves are relatively insoluble in water, they are preferably dissolved in a suitable inert organic solvent carrier. Advantageously, the solvent carrier is immiscible with water so that an emulsion of the solvent carrier in water can be prepared. If, for example, a water-miscible solvent carrier such as ethanol is used, the solvent carrier will dissolve in the water and any excess of compounds of Formula I will be thrown out of the solution. In an oil-in-water emulsion, the solvent phase is dispersed in the water phase and the dispersed phase contains the active ingredient. In this way, uniform distribution of water insoluble active ingredient is achieved in an aqueous spray. A solvent carrier in which the new compounds of Formula I are highly soluble is desirable so that relatively high concentrations of active ingredient can be obtained. Sometimes, one or more solvent carriers with or without a cosolvent can be used in order to obtain concentrated solutions of the active ingredient, the main consideration being to employ a water-immiscible solvent for the active ingredient that will hold the compound in solution over the range of concentrations useful for applying to insects and mites.

The emulsifiable concentrates of the invention are prepared, therefore, by dissolving the active ingredient and a surfactant in a substantially water-immiscible solvent carrier (i.e., a solvent carrier which is soluble in water to the extent of less than 2.5% by volume at temperatures on the order of 20° to 30° C.), for example, cyclohexanone, methyl propyl ketone, summer oils, ethylene dichloride, aromatic hydrocarbons such as benzene, toluene, and xylene, and high-boiling petroleum hydrocarbons such as kerosene, diesel oil, and the like. If desired, a cosolvent such as methyl ethyl ketone, acetone, isopropanol, and the like can be included with a solvent carrier in order to enhance the solubility of the active ingredient. Aqueous emulsions are then prepared by mixing with water to give any desired concentration of active ingredient. The surfactants which can be employed in the aqueous emulsions of the invention are those types noted above. Mixtures of surfactants can be employed, if desired.

Advantageously, the concentration of active ingredient in the emulsifiable concentrates can range from about 5% to about 50% by weight, preferably from about 10% to about 40%. A concentrate comprising 20% (by weight) of the compound dissolved in a water-immiscible solvent of the kind noted above can be admixed with an aqueous medium in the proportions of 13 ml. of concentrate with 1 gallon of medium to give a mixture containing 700 parts of active ingredient per million parts of liquid carrier. Similarly, 1 quart of a 20% concentrate mixed with 40 gallons of water provides about 1200 ppm (parts per million) of active ingredient. In the same manner, more concentrated solutions of active ingredient can be prepared.

The concentrate formulations of the invention which are intended for use in the form of aqueous dispersions of emulsions can also comprise a humectant, that is to say, an agent which will delay the drying of the composition in contact with material to which it is has been applied. Suitable humectants include glyceroll, diethylene glycol, solubilized lignins, such as calcium ligninsulfonate, and the like.

The granular formulations of this invention are convenient for application to soil when persistence is desired. Granulars are readily applied by broadcast or by localized, e.g, in-the-row, applications. The individual granules may be any desired size from 10 to 60 mesh, advantageously 20 to 40 mesh. Granulars are prepared by dissolving the active compound in a solvent such as methylene chloride, xylene, or acetone and applying the solution to a quantity of a granulated absorbent carrier. Representative granulated absorbent carriers include ground corn cobs, ground walnut shells, ground peanut hulls, and the like. If desired, the impregnated granulated absorbent carrier can be coated with a coating that will preserve the integrity of the granular until it is applied to an object or situs favorable for release of the active ingredient.

The rates of application to insects, mites, soil, or other situs will depend upon the species of the pest organism to be controlled, the presence or absence of desirable living organisms, temperature conditions of treatment, and the method and efficiency of application. In general, insecticidal and miticidal activity is obtained when the compounds are applied at concentrations of about 1 to about 5000 ppm, preferably at concentrations of about 50 to about 1200 ppm.

The formulations containing new 3-benzoyl-1-phenylthioureas of Formula I according to the invention, can be applied to insects, mites, nematodes, soil or other situs by conventional methods. For example, an area of soil, a building, or plants can be treated by applying a wettable powder from a hand-operated knapsack sprayer. Dips can be used for livestock. Dusts can be applied by powder dusters, or by hand-operated dusters. Creams and ointment formulatons can be applied to skin or objects for prolonged protection from insects or mites.

The active compounds of the invention can also be formulated in relatively dilute proportions in a dispersible insecticide carrier for household applications. Thus, the active compounds can be formulated in dusts having from about 0.1% to 5.0% active ingredient with deodorized kerosene for aerosol applications.

It will, of course, be appreciated that the conditions encountered when applying the method and formulations of this invention to actual practice can vary widely. Included among the variables that may be encountered are the degree of infestation by pests, the particular pest to be controlled, the particular situs being treated, the type of plants, the prevailing weather conditions, such as temperature, relative humidity, rainfall, dews, and so forth.

I claim:

1. New 1-aryl-3-benzoyl-2-thioureas of the formula

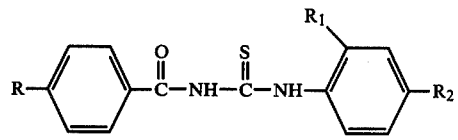

wherein R is hydrogen; and $R_1$ is lower alkyl of from one to four carbon atoms, inclusive and $R_2$ is selected from the group consisting of bromo and chloro.

2. A compound according to claim 1 wherein $R_1$ is methyl and $R_2$ is chloro so that the specific embodiment is 3-benzoyl-1-(4-chloro-2-methylphenyl)-2-thiourea.

3. A compound according to claim 1 wherein $R_1$ is methyl, $R_2$ is bromo so that the specific embodiment is 3-benzoyl-1-(4-bromo-2-methylphenyl)-2-thiourea.

4. A formulation for insect, mite and nematode control comprising a dispersible inert carrier and an insect, mite, or nematode pesticidally effective amount of a compound having the formula

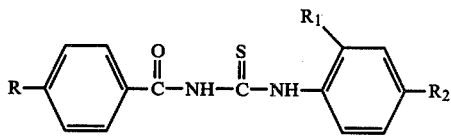

wherein R is hydrogen; and $R_1$ is lower alkyl of from one to four carbon atoms, inclusive and $R_2$ is selected from the group consisting of bromo and chloro.

5. A formulation according to claim 4 wherein $R_1$ is methyl and $R_2$ is chloro so that the specific embodiment is 3-benzoyl-1-(4-chloro-2-methylphenyl)-2-thiourea.

6. A formulation according to claim 4 wherein $R_1$ is methyl and $R_2$ is bromo so that the specific embodiment is 3-benzoyl-1-(4-bromo-2-methylphenyl)-2-thiourea.

7. A method of controlling insect pests which comprises contacting susceptible insect pests with a pesticidally effective amount of a compound having the formula

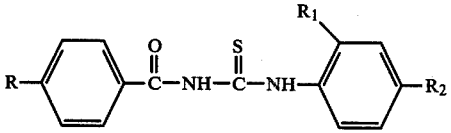

wherein R is hydrogen; and $R_1$ is lower alkyl of from one to four carbon atoms, inclusive, and $R_2$ is selected from the group consisting of bromo and chloro.

8. A method according to claim 7 wherein $R_1$ is methyl and $R_2$ is chloro so that the specific embodiment is 3-benzoyl-1-(4-chloro-2-methylphenyl)-2-thiourea.

9. A method according to claim 7 wherein $R_1$ is methyl and $R_2$ is bromo so that the specific embodiment is 3-benzoyl-1-(4-bromo-2-methylphenyl-2-thiourea.

* * * * *